US010085897B2

United States Patent
Landgrebe et al.

(10) Patent No.: US 10,085,897 B2
(45) Date of Patent: Oct. 2, 2018

(54) FASTENING SYSTEMS FOR USE WITH ABSORBENT ARTICLES

(71) Applicant: The Procter & Gamble Company, Cincinnati, OH (US)

(72) Inventors: James David Landgrebe, Madeira, OH (US); Joerg Mueller, Karben (DE); Darren Lee Goad, Cold Spring, KY (US); Markus Rosar, Schwalbach (DE); Thomas Tombuelt-Meyer, Nettersheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 905 days.

(21) Appl. No.: 14/180,559

(22) Filed: Feb. 14, 2014

(65) Prior Publication Data

US 2014/0236115 A1    Aug. 21, 2014

Related U.S. Application Data

(60) Provisional application No. 61/765,333, filed on Feb. 15, 2013.

(51) Int. Cl.
*A61F 13/15* (2006.01)
*A61F 13/20* (2006.01)
(Continued)

(52) U.S. Cl.
CPC ........ *A61F 13/56* (2013.01); *A61F 13/15699* (2013.01); *A61F 13/5633* (2013.01);
(Continued)

(58) Field of Classification Search
CPC .. A61F 13/56; A61F 13/622; A61F 13/15699; A61F 13/5633; A61F 13/563
See application file for complete search history.

(56) References Cited

U.S. PATENT DOCUMENTS

| 3,848,594 A | 11/1974 | Buell |
| 3,860,003 A | 1/1975 | Buell |

(Continued)

FOREIGN PATENT DOCUMENTS

| EP | 0149880 A2 | 7/1985 |
| FR | 2807939 A1 | 8/2002 |

(Continued)

OTHER PUBLICATIONS

International Search Report and Written Opinion, PCT/US2014/016337, dated May 8, 2014.
All Office Actions, U.S. Appl. No. 14/180,572.

*Primary Examiner* — Michele M Kidwell
(74) *Attorney, Agent, or Firm* — William E. Gallagher; Christian M. Best

(57) ABSTRACT

A fastener for a disposable absorbent article, having a fixed portion attachable to the article, a connective portion joined to and contiguous with the fixed portion, and a folding line disposed between the fixed and connective portions. The fastener may be free of a release tape. The fastener may further comprise an adhesive disposed upon a surface of the fixed portion of the fastener being attached to the article, the adhesive being offset from each of the edges of the fixed portion including the edge formed by the folding line, the dimensions of the offsets being defined herein. The adhesive may be applied during the assembly of the absorbent article on a converting line.

37 Claims, 8 Drawing Sheets

(51) Int. Cl.
*A61F 13/56* (2006.01)
*A61F 13/62* (2006.01)

(52) U.S. Cl.
CPC ........ *A61F 13/5638* (2013.01); *A61F 13/622* (2013.01); *Y10T 29/49966* (2015.01); *Y10T 156/10* (2015.01)

(56) References Cited

U.S. PATENT DOCUMENTS

| | | | |
|---|---|---|---|
| 4,430,148 A | 2/1984 | Schaefer | |
| 4,610,678 A | 9/1986 | Weisman et al. | |
| 4,662,875 A | 5/1987 | Hirotsu et al. | |
| 4,823,783 A | 4/1989 | Willhite et al. | |
| 4,834,735 A | 5/1989 | Alemany et al. | |
| 4,846,815 A | 7/1989 | Scripps | |
| 4,888,231 A | 12/1989 | Angstadt | |
| 4,894,060 A | 1/1990 | Nestegard | |
| 4,940,464 A | 7/1990 | Van Gompel et al. | |
| 4,946,527 A | 8/1990 | Battrell | |
| 5,019,065 A | 5/1991 | Scripps | |
| 5,037,416 A | 8/1991 | Allen et al. | |
| 5,053,028 A | 10/1991 | Zoia et al. | |
| 5,092,861 A | 3/1992 | Nomura et al. | |
| 5,137,537 A | 8/1992 | Herron et al. | |
| 5,151,092 A | 9/1992 | Buell et al. | |
| 5,221,274 A | 6/1993 | Buell et al. | |
| 5,246,433 A | 9/1993 | Hasse et al. | |
| 5,260,345 A | 11/1993 | Desmarais et al. | |
| 5,269,775 A | 12/1993 | Freeland et al. | |
| 5,387,207 A | 2/1995 | Dyer et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,578,152 A | 11/1996 | Goulait et al. | |
| 5,624,429 A | 4/1997 | Long | |
| 5,625,222 A | 4/1997 | Yoneda et al. | |
| 5,897,545 A | 4/1999 | Kline et al. | |
| 5,957,908 A | 9/1999 | Kline et al. | |
| 5,961,761 A | 10/1999 | Heindel et al. | |
| 6,004,306 A | 12/1999 | Roe et al. | |
| 6,030,373 A | 2/2000 | VanGompel et al. | |
| 6,063,466 A | 5/2000 | Tuschy et al. | |
| 6,120,487 A | 9/2000 | Ashton et al. | |
| 6,120,489 A | 9/2000 | Johnson et al. | |
| 6,251,097 B1 | 6/2001 | Kline et al. | |
| 6,432,098 B1 | 8/2002 | Kline et al. | |
| 6,645,569 B2 | 11/2003 | Rohrbaugh et al. | |
| 6,669,618 B2 | 12/2003 | Reising et al. | |
| 6,863,933 B2 | 3/2005 | Rohrbaugh et al. | |
| 7,112,621 B2 | 9/2006 | Rohrbaugh et al. | |
| 7,578,813 B2 | 8/2009 | Mitsui et al. | |
| 7,896,858 B2 * | 3/2011 | Trennepohl ....... A61F 13/15699 | 604/385.01 |
| 8,168,853 B2 | 5/2012 | Autran et al. | |
| 8,193,407 B2 | 6/2012 | Mansfield et al. | |
| 8,226,626 B2 | 7/2012 | Turner et al. | |
| 8,496,640 B2 | 7/2013 | Molander | |
| 9,072,634 B2 | 7/2015 | Hundorf et al. | |
| 2003/0045854 A1 | 3/2003 | Yoshioka | |
| 2003/0105190 A1 | 6/2003 | Diehl et al. | |
| 2003/0148684 A1 | 8/2003 | Cramer et al. | |
| 2003/0233082 A1 | 12/2003 | Kline et al. | |
| 2004/0022998 A1 | 2/2004 | Miyamoto | |
| 2004/0158212 A1 | 8/2004 | Ponomarenko et al. | |
| 2004/0181200 A1 | 9/2004 | Desai et al. | |
| 2004/0193133 A1 | 9/2004 | Desai et al. | |
| 2005/0008839 A1 | 1/2005 | Cramer et al. | |
| 2006/0069377 A1 | 3/2006 | Calvert | |
| 2006/0129121 A1 * | 6/2006 | Erdman ............ A61F 13/5622 | 604/389 |
| 2006/0212018 A1 * | 9/2006 | Roe .................. A61F 13/496 | 604/389 |
| 2006/0287637 A1 | 12/2006 | Lam | |
| 2007/0078427 A1 | 4/2007 | Raycheck et al. | |
| 2007/0093769 A1 | 4/2007 | Kline et al. | |
| 2007/0219521 A1 | 9/2007 | Hird et al. | |
| 2008/0097368 A1 | 4/2008 | Molander | |
| 2008/0312617 A1 | 12/2008 | Hundorf et al. | |
| 2008/0312625 A1 | 12/2008 | Hundorf et al. | |
| 2009/0292270 A1 * | 11/2009 | Showole ............. A61F 13/58 | 604/390 |
| 2010/0036339 A1 | 2/2010 | Hammons et al. | |
| 2010/0036347 A1 | 2/2010 | Hammons et al. | |
| 2010/0036349 A1 | 2/2010 | Hammons et al. | |
| 2010/0191211 A1 | 7/2010 | Molander | |
| 2010/0280484 A1 | 11/2010 | Kline et al. | |
| 2011/0073513 A1 * | 3/2011 | Weisman ............. A61F 13/53 | 206/494 |
| 2011/0100526 A1 | 5/2011 | Umebayashi | |
| 2011/0139657 A1 | 6/2011 | Hird et al. | |
| 2011/0139658 A1 | 6/2011 | Hird et al. | |
| 2011/0139659 A1 | 6/2011 | Hird et al. | |
| 2011/0139662 A1 | 6/2011 | Hird et al. | |
| 2011/0152812 A1 | 6/2011 | Hird et al. | |
| 2012/0245548 A1 | 9/2012 | Matsushima | |

FOREIGN PATENT DOCUMENTS

| | | |
|---|---|---|
| JP | 402541 B2 | 12/2007 |
| WO | WO 95/16746 A1 | 6/1995 |
| WO | WO 1997-26851 A1 | 7/1997 |
| WO | WO 02/064877 A2 | 8/2002 |
| WO | WO 05/110731 A2 | 11/2005 |
| WO | WO 2012/129428 A1 | 9/2012 |

* cited by examiner

FASTENING SYSTEMS FOR USE WITH ABSORBENT ARTICLES

TECHNICAL FIELD

The present disclosure relates to fastening systems for use with wearable absorbent articles, and more particularly relates to fastening systems having certain fastening tapes that improve the fit of such articles about a wearer and/or reduce the cost of manufacturing such articles, wherein such systems may be refastenable.

BACKGROUND

The use of fastening systems for securing the corners of disposable absorbent articles, such as diapers, is known. Such systems are used to provide a secure means for keeping such articles on the wearer during use. When such systems are refastenable, adjustments may be made during use to reposition the articles, to allow a caregiver to check for soiling, and may also be used to provide a secure means for keeping such articles and their soiled contents wrapped up after use until disposal.

A typical fastening system for use with absorbent articles may have a fastening tape and a landing member (also known as a landing zone). The fastening tape may be disposed directly or indirectly upon the longitudinal edge of the body portion in either the front or back of the absorbent article waist regions. In use, the fastening tape may be secured to the landing member, which is disposed upon the correspondingly opposite body portion of the front or back of the absorbent article. A refastenable system may be provided with, e.g., hooks on the fastening tape that releasably engage loops disposed on the landing member, or vice versa. To improve fit, the end of the fastening tape that does not engage the loops in the landing member area, may be attached to one end of an elastic/stretch member (ear), and the other end of the elastic/stretch member may be secured to the longitudinal edge of the body portion of the absorbent article.

Manufacturers of absorbent articles, e.g. diapers, typically employ mechanical assembly lines in which a variety of absorbent article components are fed into a linear process whereby each step builds upon the last one. Such assembly lines are often referred to as "converters". As the partial absorbent article progresses towards the end of the converter, it becomes more complete, until at the end of the line, all the necessary parts have been provided and arranged as needed to yield a completely assembled absorbent article. The process is typically automated and may be controlled by various computer programs and/or human operators, as desired. In order to make the manufacture of absorbent articles economically viable, such converting lines must be capable of operating at high speeds with good repeatability and consistency between consecutive articles. Two elements that impact economic viability are the nature of the absorbent article components and how they will be attached to other components to form a completely assembled absorbent article, and the material cost of each absorbent article component.

The inventors have observed that conventional fastening tapes that are provided into the assembly line having already been coated with an adhesive prior to being provided to the line will typically be such that the adhesive covers all of the portion of the tape that is to overlap the ear to which the tape will be connected, and there is a certain cost associated with this arrangement. If the adhesive is applied continuously online, the adhesive's properties can change during line stops if there is a large physical gap between the adhesive application point and the usage point. Also, the adhesive may tend to contaminate the knives used to separate individual tapes from the incoming tape web. Additionally, an element of the cost is that a release tape is typically required to be used in combination with such an arrangement because adhesive is exposed. If a pressure-sensitive adhesive is to be applied online, additional expensive and space-consuming equipment may be required to deliver it onto the product in addition to the construction adhesive equipment typically present on converters for disposable articles.

Attempts to achieve good fit and/or to reduce manufacturing cost have been made previously; however, there is a need to improve over these. For example, U.S. Pat. No. 5,019,065 (Scripps) discloses a fastening tape that combines a mechanical mechanism, e.g. hook and loop, with an exposed adhesive that secures the tape tab to a body portion of an absorbent article to provide a side closure and also secures the absorbent article in its disposal configuration. The exposed adhesive is preferably a pressure-sensitive adhesive and a release tape may be employed to achieve releaseability. A similar fastening system is disclosed in U.S. Pat. No. 5,053,028 (Zoia, et al.), wherein the use of a pressure-sensitive adhesive as the exposed adhesive and the use of a release tape are both overtly required. Further, WO 2012/129428A1 (Bogaerts, et al.) discloses a fastening tape having a patterned adhesive where certain regions of tape surface have adhesive present while others do not, in combination with a release tape.

Generally, the use of pressure-sensitive adhesives may either restrict the tape tab stock to be pre-manufactured and supplied to the converter on rolls or it may necessitate the installation of expensive and complicated adhesive dispensing equipment to augment the typical construction adhesives found on absorbent article converters. Generally, the presence of a release tape adds complexity and cost to the manufacturing process versus fastening systems that omit such a feature. As such, there is a need for fastening systems that provide improved fit to the wearers of absorbent articles and/or reduce the cost of manufacturing such articles.

SUMMARY

A fastener for a disposable absorbent article, having a fixed portion attachable to the article, a connective portion joined to and contiguous with the fixed portion, and a folding line disposed between the fixed and connective portions. The fastener may be free of a release tape. The fastener may further comprise an adhesive disposed upon a surface of the fixed portion of the fastener being attached to the article, the adhesive being offset from each of the edges of the fixed portion including the edge formed by the folding line, the dimensions of the offsets being defined herein. The adhesive may be applied during the assembly of the absorbent article on a converting line. The fasteners provide improved fit to the wearers of absorbent articles and/or reduce the cost of manufacturing such articles.

In an embodiment, a disposable absorbent article comprising a body portion and a fastener, the body portion comprising a liquid pervious topsheet, a liquid impervious backsheet joined to the topsheet, and a core disposed between the topsheet and the backsheet, the core being substantially cellulose free; the fastener comprising: a fixed portion attached to the article, an adhesive being disposed upon a surface of the fixed portion of the fastener attached to the article; a connective portion joined to and contiguous with the fixed portion, the connective portion comprising: a distal edge; a fastening member having a fastening surface and a bonding surface opposite to the fastening surface, wherein the fastening surface is releasably fastenable to the article; a backing member attached to the bonding surface of the fastening member; and a folding line disposed between the fixed and connective portions; wherein the adhesive is disposed upon the fixed portion of the fastener such that it is offset from each of the inboard and outboard edges (CD) of the fixed portion that are overlapped by the body portion.

DETAILED DESCRIPTION

Definitions

Figure 1:
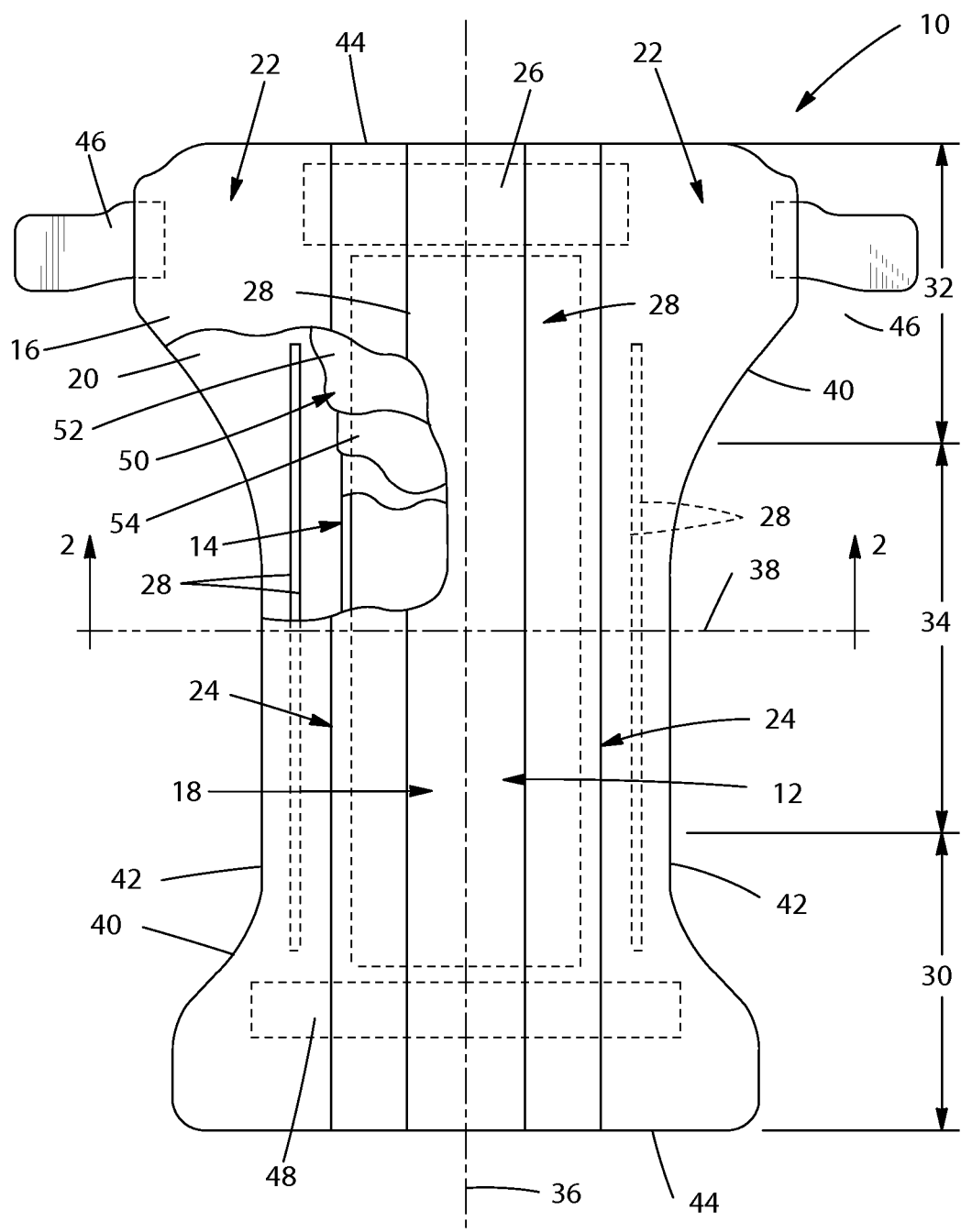
FIG. 1 is a plan view of a diaper.

The following term explanations may be useful in understanding the present disclosure.

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

"Absorbent core" means a structure that may be disposed between a topsheet and backsheet of an absorbent article for absorbing and containing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core may be substantially cellulose free. The absorbent core does not include an acquisition system, a topsheet, or a backsheet of the absorbent article.

"Absorbent polymer material," "absorbent gelling material," "AGM," "superabsorbent," and "superabsorbent material" are used interchangeably and refer to cross linked polymeric materials that can absorb at least 5 times their weight of an aqueous 0.9% saline solution as measured using the Centrifuge Retention Capacity test (Edana 441.2-01).

"Absorbent particulate polymer material" means an absorbent polymer material which is in particulate form so as to be flowable in the dry state.

"Absorbent particulate polymer material area" means the area of the core wherein the first substrate and second substrate are separated by a multiplicity of superabsorbent particles. There may be some extraneous superabsorbent particles outside of this area between the first substrate 64 and second substrate.

"Activation" means any process by which tensile strain produced by intermeshing teeth and grooves causes intermediate web sections to stretch or extend. Such processes have been found useful in the production of many articles including breathable films, stretch composites, apertured materials and textured materials. For nonwoven webs, the stretching can cause fiber reorientation, change in fiber denier and/or cross section, a reduction in basis weight, and/or controlled fiber destruction in the intermediate web sections. For example, a common activation method is the process known in the art as ring rolling.

"Airfelt" means comminuted wood pulp, which is a form of cellulosic fiber.

"Basis weight" means the mass of dry fibrous material per unit area, i.e. the mass of dry sheet per unit area, e.g. gram per square meter (gsm).

"Body facing surface" and "body facing side" refer to surfaces of absorbent articles and/or components thereof which face a wearer's body when the absorbent articles are worn, and the term "garment facing surface" and "garment facing side" refer to surfaces of absorbent articles and/or components thereof that face away from a wearer's body when the absorbent articles are worn. Absorbent articles and components thereof, including the topsheet, backsheet, absorbent core, and any individual materials of their components, have a body facing surface and/or side and a garment facing surface and/or side.

"Bicomponent fibers" means fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used to limit the scope of subject matter, such as that in a claim, to the specified materials or steps and those that do not materially affect the basic and novel characteristics of the subject matter.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" means an absorbent article generally worn by infants and incontinent persons about the lower torso so as to encircle the waist and legs of the wearer and that is specifically adapted to receive and contain urinary and fecal waste. As used herein, term "diaper" also includes a "pant" which is defined below.

"Fiber" and "filament" are used interchangeably.

"Film" means a skin-like or membrane-like layer of material formed of one or more polymers, which does not have a form consisting predominately of a web-like structure of consolidated polymer fibers and/or other fibers.

"Inboard", and forms thereof, with respect to features of a fastener, means furthest from or in a direction away from the free distal end.

"Joined" is meant to encompass configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" means a direction running from a longitudinally extending side edge to a laterally opposing longitudinally extending side edge of an article and generally at a right angle to the longitudinal direction. Directions within 45 degrees of the lateral direction are considered to be "lateral."

"Machine direction" (MD) means the direction of material flow through a process. In addition, relative placement and movement of material can be described as flowing in the machine direction through a process from upstream in the process to downstream in the process. "Cross direction" (CD) means a direction that is generally perpendicular to the machine direction. "Z-direction," with respect to a web, means generally orthogonal or perpendicular to the plane approximated by the web along the machine and cross direction dimensions.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Outboard", and forms thereof, with respect to features of a fastener, means at or in a direction toward its free distal end.

"Pant" or "training pant" means disposable garments having a waist opening and leg openings designed for infant or adult wearers. A pant may be placed in position on the wearer by inserting the wearer's legs into the leg openings and sliding the pant into position about a wearer's lower torso. A pant may be pre-formed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

A "pressure-sensitive adhesive" is a self-stick adhesive that adheres when pressure is applied to connect the substrate on which the adhesive is applied to another substrate or object, e.g. an absorbent article component. This adhesion occurs without the need for introducing solvents or heating to bring about a phase change. The phase change requirement differentiates pressure-sensitive adhesives from hot-melt adhesives, which require a phase change to activate them. Adhesion of pressure-sensitive adhesives can be enhanced by warming to a temperature less than that which would cause a phase change that liquefies the adhesive.

The term "shedable nonwoven" refers to a nonwoven fabric having a base nonwoven fabric and a surface of fibers loosely bonded to the base nonwoven fabric. When the surface fibers are removed, the base nonwoven fabric typically retains about 70% or more of its tensile strength properties.

"Substantially cellulose free" means an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core.

"Substantially continuously distributed" indicates that within the absorbent particulate polymer material area, the first substrate 64 and second substrate 72 are separated by a multiplicity of superabsorbent particles. It is recognized that there may be minor incidental contact areas between the first substrate 64 and second substrate 72 within the absorbent particulate polymer material area. Incidental contact areas between the first substrate 64 and second substrate 72 may be intentional or unintentional (e.g. manufacturing artifacts) but do not form geometries such as pillows, pockets, tubes, quilted patterns and the like.

"Tensile Strength" refers to the maximum tensile force (Peak Force) a material will sustain before tensile failure, as measured by the Tensile Strength Measurement Method set forth herein.

"Thermoplastic adhesive material" is understood to comprise a polymer composition from which fibers are formed and applied to the superabsorbent material with the intent to immobilize the superabsorbent material in both the dry and wet state. The thermoplastic adhesive material of the present disclosure forms a fibrous network over the superabsorbent material.

"Thickness" and "caliper" are used herein interchangeably.

In some embodiments, the absorbent article is a diaper. For convenience, an exemplary absorbent article will be described using a diaper as a reference. The skilled person will appreciate that other absorbent articles can also be assembled with topsheets and associated components as disclosed herein.

FIG. 1 is a plan view of a diaper 10, shown in a flat out, uncontracted state (i.e., without elastic induced contraction) and with portions of the diaper 10 are cut away to more clearly show the underlying structure of the diaper 10. A portion of the diaper 10 that contacts a wearer is facing the viewer in FIG. 1. The diaper 10 generally may include a chassis 12 and an absorbent core 14 disposed in the chassis.

The chassis 12 of the diaper 10 in FIG. 1 may include an outer covering 16 including a topsheet 18, which may be liquid pervious, and/or a backsheet 20, which may be liquid impervious. The absorbent core 14 may be encased between the topsheet 18 and the backsheet 20. The chassis 12 may also include side panels 22, elasticized leg cuffs 24, and an elastic waist feature 26.

The leg cuffs 24 and the elastic waist feature 26 may each include elastic members 28. One end portion of the diaper 10 may be configured as a first waist region 30 of the diaper 10. An opposite end portion of the diaper 10 may be configured as a second waist region 32 of the diaper 10. An intermediate portion of the diaper 10 may be configured as a crotch region 34, which extends longitudinally between the first and second waist regions 30 and 32. The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 is depicted in FIG. 1 with a longitudinal axis 36 and a transverse axis 38. The periphery 40 of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper 10. The chassis 12 may also comprise a fastening system, which may include at least one fastener 46 and optionally, at least one stored landing zone 48. In an embodiment, fastener 46 may be fastened directly to backsheet 20.

The diaper 20 may also include such other features as are known in the art including front and rear ear panels, waist cap features, elastics and the like to provide better fit, as well as containment and aesthetic characteristics. Such additional features are described, for example, in U.S. Pat. Nos. 3,860,003 and 5,151,092.

In order to keep the diaper 10 in place about the wearer, at least a portion of the first waist region 30 may be attached by the fastener 46 to at least a portion of the second waist region 32 to form leg opening(s) and an article waist opening. When fastened, the fastening system carries a tensile load around the article waist. The fastening system may allow an article user to hold one element of the fastening system, such as the fastener 46, and connect the first waist region 30 to the second waist region 32 in at least two places. This may be achieved through manipulation of bond strengths between the fastening device elements.

Fastener 46 is adapted to refastenably connect with the first waist region 30. As such, the fastener 46 may include various types of refastenably engageable fasteners and various types of refastenable fastening structures. For example, fastener 46 may include mechanical fasteners, in the form of hook and loop fasteners, hook and hook fasteners, macrofasteners, buttons, snaps, tab and slot fasteners, tape fasteners, adhesive fasteners, cohesive fasteners, magnetic fasteners, hermaphroditic fasteners, and the like. Some examples of fastening systems and/or fastening components are discussed in U.S. Pat. Nos. 3,848,594; 4,662,875; 4,846,815; 4,894,060; 4,946,527; 5,151,092; 5,221,274; 6,251,097; 6,669,618; 6,432,098; and U.S. Patent Publication Nos. 2007/0078427 and 2007/0093769.

In some embodiments, the diaper 10 may be provided with a re-closable fastening system or may alternatively be provided in the form of a pant-type diaper. When the absorbent article is a diaper, it may include a re-closable fastening system joined to the chassis for securing the diaper to a wearer. When the absorbent article is a pant-type diaper, the article may include at least two side panels joined to the chassis and to each other to form a pant. The fastening system and any component thereof may include any material suitable for such a use, including but not limited to plastics, films, foams, nonwoven, woven, paper, laminates, fiber reinforced plastics and the like, or combinations thereof. In some embodiments, the materials making up the fastening device may be flexible. The flexibility may allow the fastening system to conform to the shape of the body and thus, reduce the likelihood that the fastening system will irritate or injure the wearer's skin.

It is to be appreciated that the topsheet 18, the backsheet 20, and the absorbent core 14 may be assembled in a variety of configurations, such as for example as described generally in U.S. Pat. Nos. 5,554,145; 5,569,234; and 6,004,306. Processes for assembling the diaper include conventional techniques known in the art for constructing and configuring disposable absorbent articles. For example, the backsheet and/or the topsheet can be joined to the absorbent core or to each other by a uniform continuous layer of adhesive, a patterned layer of adhesive, or an array of separate lines, spirals, or spots of adhesive. Adhesives which have been found to be satisfactory are manufactured by H.B. Fuller Company (St. Paul, Minn.) under the designation HL-1258 or H-2031.

In some embodiments, the topsheet 18 in FIG. 1 may be fully or partially elasticized or may be foreshortened to provide a void space between the topsheet 18 and the absorbent core 14. Exemplary structures including elasticized or foreshortened topsheets are described in more detail in U.S. Pat. Nos. 5,037,416 and 5,269,775.

The backsheet 26 may be joined with the topsheet 18. The backsheet 20 may prevent the exudates absorbed by the absorbent core 14 and contained within the diaper 10 from soiling other external articles that may contact the diaper 10, such as bed sheets and undergarments. In certain embodiments, the backsheet 26 may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind., and sold under the trade names X15306, X10962, and X10964. Other suitable backsheet materials may include breathable materials that permit vapors to escape from the diaper 10 while still preventing liquid exudates from passing through the backsheet 10. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E.I. DuPont. Other breathable backsheets including nonwoven webs and apertured formed films are described in U.S. Pat. No. 5,571,096.

Figure 2:
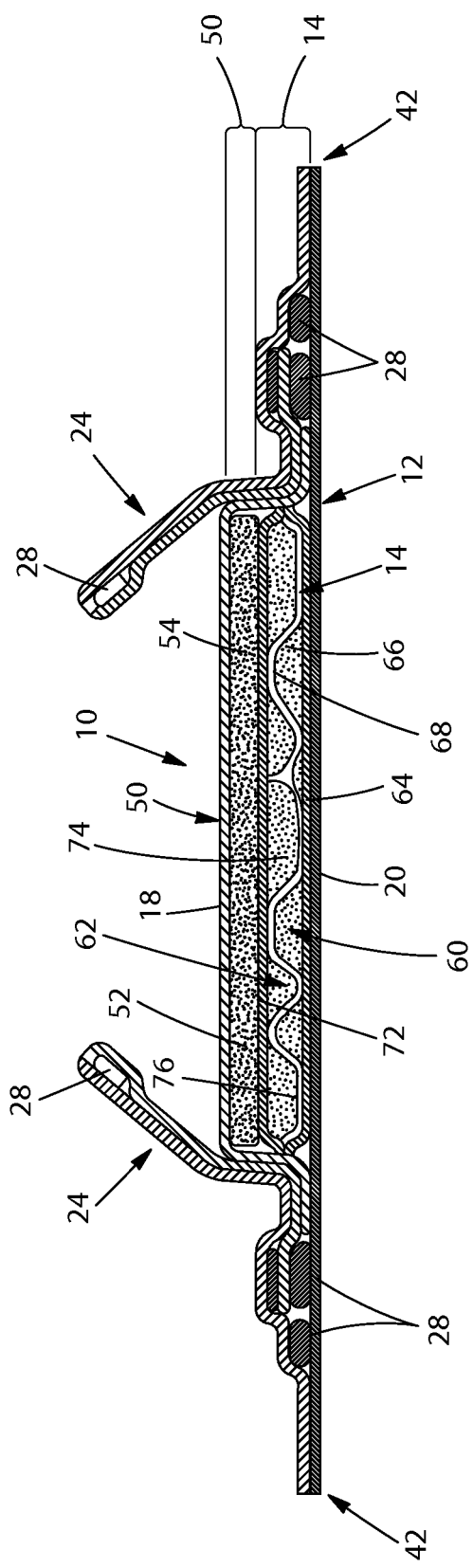
FIG. 2 is a cross sectional view of the diaper shown in FIG. 1 taken along the sectional line 2-2 of FIG. 1.

FIG. 2 is a cross sectional view of the diaper taken along the line 2-2 in FIG. 1. As shown in FIG. 2, the topsheet 18 may define an inner, body facing surface, and the backsheet may define an outer, garment facing surface of the diaper 10. And the absorbent core 14 may be positioned between the topsheet and the backsheet. The diaper 10 may also include an acquisition system 50 disposed between the liquid permeable topsheet 18 and a wearer facing side of the absorbent core 14. The acquisition system 50 may be in direct contact with the absorbent core. The acquisition system 50 (also referred to herein as a liquid acquisition layer 50) may comprise a single layer or multiple layers, such as an upper acquisition layer 52 (also referred to herein as a first acquisition layer 52) facing towards the wearer's skin and a lower acquisition layer 54 (also referred to herein as a second acquisition layer 54) facing the garment of the wearer. In some embodiments, the acquisition system 50 may function to receive a surge of liquid, such as a gush of urine. In other words, the acquisition system 50 may serve as a temporary reservoir for liquid until the absorbent core 14 can absorb the liquid.

In some embodiments, the acquisition system 50 may include chemically cross-linked cellulosic fibers. Such cross-linked cellulosic fibers may have desirable absorbency properties. Exemplary chemically cross-linked cellulosic fibers are disclosed in U.S. Pat. No. 5,137,537. In certain embodiments, the chemically cross-linked cellulosic fibers are cross-linked with between 0.5 mole % and 10.0 mole % of a $C_2$ to $C_9$ polycarboxylic cross-linking agent or between 1.5 mole % and 6.0 mole % of a $C_2$ to $C_9$ polycarboxylic cross-linking agent based on glucose unit. Citric acid is an exemplary cross-linking agent. In some embodiments, polyacrylic acids may be used. Further, according to some embodiments, the cross-linked cellulosic fibers have a water retention value of 25 to 60, or 28 to 50, or 30 to 45. A method for determining water retention value is disclosed in U.S. Pat. No. 5,137,537. In some embodiments, the cross-linked cellulosic fibers may be crimped, twisted, or curled, or a combination thereof including crimped, twisted, and curled.

In some embodiments, one or both of the upper acquisition layer 52 and lower acquisition layer 54 may include a nonwoven, which may be hydrophilic. Further, according to some embodiments, one or both of the upper acquisition layer 52 and lower acquisition layer 54 may comprise the chemically cross-linked cellulosic fibers, which may or may not form part of a nonwoven material. In some embodiments, the upper acquisition layer 52 may comprise a nonwoven, without the cross-linked cellulosic fibers, and the lower acquisition layer 54 may comprise the chemically cross-linked cellulosic fibers. Further, in some embodiments, the lower acquisition layer 54 may comprise the chemically cross-linked cellulosic fibers mixed with other fibers such as natural or synthetic polymeric fibers. According to some embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof. In some embodiments, the lower acquisition layer 54 has a total dry weight, the cross-linked cellulosic fibers are present on a dry weight basis in the upper acquisition layer in an amount from 30% to 95% by weight of the lower acquisition layer 54, and the other natural or synthetic polymeric fibers are present on a dry weight basis in the lower acquisition layer 54 in an amount from 70% to 5% by weight of the lower acquisition layer 54. According to some embodiments, the cross-linked cellulosic fibers are present on a dry weight basis in the first acquisition layer in an amount from 80% to 90% by weight of the lower acquisition layer 54, and the other natural or synthetic polymeric fibers are present on a dry weight basis in the lower acquisition layer 54 in an amount from 20% to 10% by weight of the lower acquisition layer 54.

For example, in some embodiments, the lower acquisition layer 54 may comprise 70% by weight of chemically cross-linked cellulose fibers, 10% by weight polyester (PET), and 20% by weight untreated pulp fibers. According to a second embodiment, the lower acquisition layer 54 may comprise 70% by weight chemically cross-linked cellulose fibers, 20% by weight lyocell fibers, and 10% by weight PET fibers. According to a third embodiment, the lower acquisition layer 54 may comprise 68% by weight chemically cross-linked cellulose fibers, 16% by weight untreated pulp fibers, and 16% by weight PET fibers. In one embodiment, the lower acquisition layer 54 may comprise from 90-100% by weight chemically cross-linked cellulose fibers.

Suitable nonwoven materials for the upper acquisition layer 52 and lower acquisition layer 54 include, but are not limited to SMS material, comprising a spunbonded, a meltblown and a further spunbonded layer. In certain embodiments, permanently hydrophilic nonwovens, and in particular, nonwovens with durably hydrophilic coatings are desirable. Another suitable embodiment comprises a SMMS-structure. In certain embodiments, the nonwovens are porous.

In certain embodiments, suitable nonwoven materials may include, but are not limited to synthetic fibers, such as PE, PET, and PP. As polymers used for nonwoven production may be inherently hydrophobic, they may be coated with hydrophilic coatings. One way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven as described in co-pending U.S. Patent Publication No. 2005/0159720. Another way to produce nonwovens with durably hydrophilic coatings is to coat the nonwoven with hydrophilic nanoparticles as described in U.S. Pat. No. 7,112,621 and in PCT Publication No. WO 02/064877.

Nanoparticles may have a largest dimension of below 750 nm. Nanoparticles with sizes ranging from 2 to 750 nm may be economically produced. Some nanoparticles can be easily dispersed in water solution to enable coating application onto the nonwoven, form transparent coatings, and the coatings applied from water solutions are may be sufficiently durable to exposure to water. Nanoparticles can be organic or inorganic, synthetic or natural. Inorganic nanoparticles generally exist as oxides, silicates, and/or, carbonates. Typical examples of suitable nanoparticles are layered clay minerals (e.g., LAPONITE™ from Southern Clay Products, Inc. (USA), and Boehmite alumina (e.g., Disperal P2™ from North American Sasol. Inc.). According to a certain embodiment, a suitable nanoparticle coated nonwoven is that disclosed in the U.S. Patent Publication No. 2004/0158212A1.

Other nonwovens are described in U.S. Pat. Nos. 6,645,569; 6,863,933; and 7,112,621 as well as U.S. Patent Publication Nos. 2003/0148684A1 and 2005/0008839A1.

In some cases, the nonwoven surface can be pre-treated with high energy treatment (corona, plasma) prior to application of nanoparticle coatings. High energy pre-treatment typically temporarily increases the surface energy of a low surface energy surface (such as PP) and thus enables better wetting of a nonwoven by the nanoparticle dispersion in water.

Permanently hydrophilic nonwovens may be used in other parts of an absorbent article. For example, in some embodiments, topsheets and absorbent core layers comprising permanently hydrophilic nonwovens as described above can be used.

According to some embodiments, the upper acquisition layer 52 may include a material that provides recovery when external pressure is applied and removed. Further, according to some embodiments, the upper acquisition layer 52 may comprise a blend of different fibers selected, for example from the types of polymeric fibers described above. In some embodiments, at least a portion of the fibers may exhibit a spiral-crimp which has a helical shape. In some embodiments, the upper acquisition layer 52 may comprise fibers having different degrees or types of crimping, or both. For example, embodiments may include a mixture of fibers having about 8 to about 12 crimps per inch (cpi) or about 9 to about 10 cpi, and other fibers having about 4 to about 8 cpi or about 5 to about 7 cpi. Different types of crimps include, but are not limited to a 2D crimp or "flat crimp" and a 3D or spiral-crimp. According to some embodiments, the fibers may include bi-component fibers, which are individual fibers each comprising different materials, usually a first and a second polymeric material.

The upper acquisition layer 52 may be stabilized by a latex binder, for example a styrene-butadiene latex binder (SB latex), in a certain embodiment. Processes for obtaining such lattices are known, for example, from EP Patent Publication No. EP 0149880A2 and U.S. Patent Publication No. 2003/0105190. In some embodiments, the binder may be present in the upper acquisition layer 52 in excess of about 12%, about 14% or about 16% by weight. For certain embodiments, SB latex is available under the trade name GENFLO™ 3160 (OMNOVA Solutions Inc.; Akron, Ohio).

Figure 3:
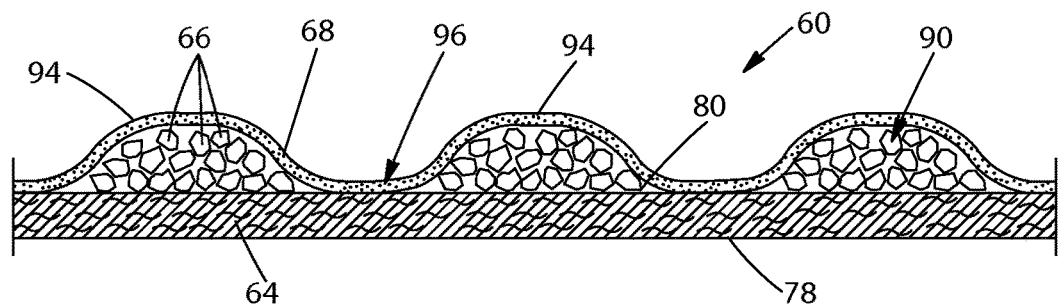
FIG. 3 is a partial cross sectional view of an absorbent core layer.

The absorbent core 14, such as shown in FIGS. 1-4, 5A, and 5B, may be disposed between the topsheet 18 and the backsheet 20 and may include two layers, a first absorbent layer 60 and a second absorbent layer 62. As shown in FIG. 3, the first absorbent layer 60 of the absorbent core 14 may include a substrate 64, an absorbent particular polymer material 66 on the substrate 64, and a thermoplastic composition 68 on the absorbent particulate polymer material 66 and at least portions of the first substrate 64 as an adhesive for covering and immobilizing the absorbent particulate polymer material 66 on the first substrate 64. According to another embodiment illustrated in FIG. 4, the first absorbent layer 60 of the absorbent core 14 may also include a cover layer 70 on the thermoplastic composition 68.

As shown in FIG. 2, the second absorbent layer 62 of the absorbent core 14 may also include a substrate 72, an absorbent particulate polymer material 74 on the second substrate 72, and a thermoplastic composition 66 on the absorbent particulate polymer material 74 and at least a portion of the second substrate 72 for immobilizing the absorbent particulate polymer material 74 on the second substrate 72. Although not illustrated, the second absorbent layer 62 may also include a cover layer such as the cover layer 70 illustrated in FIG. 4.

The substrate 64 of the first absorbent layer 60 may be referred to as a dusting layer and has a first surface 78 which faces the backsheet 20 of the diaper 10 and a second surface 80 which faces the absorbent particulate polymer material 66. The substrate 72 of the second absorbent layer 62 may be referred to as a core cover and has a first surface 82 facing the topsheet 18 of the diaper 10 and a second surface 84 facing the absorbent particulate polymer material 74. The first and second substrates 64 and 72 may be adhered to one another with adhesive about the periphery to form an envelope about the absorbent particulate polymer materials 66 and 74 to hold the absorbent particulate polymer material 66 and 74 within the absorbent core 14.

In some embodiments, the substrates 64 and 72 of the first and second absorbent layers 60 and 62 may be a nonwoven material, such as those nonwoven materials described above. In some embodiments, the nonwovens are porous and may have a pore size of about 32 microns.

The majority of currently marketed absorbent articles comprise as absorbent material a blend of comminuted wood pulp with superabsorbent polymers (SAP) in particulate form, also called absorbent gelling materials (AGM), see for example U.S. Pat. No. 5,151,092 (Buell). Absorbent articles having a core consisting essentially of SAP as absorbent material (so called "airfelt-free" cores) have also been proposed (see e.g. WO2008/155699 (Hundorf), WO95/11652 (Tanzer), WO2012/052172 (Van Malderen)). Absorbent cores with slits or grooves have also been proposed, typically to increase the fluid acquisition properties of the core or to act as a folding guide.

WO2012/170778 (Rosati et al., see also WO2012/170779, WO2012/170781 and WO2012/170808) discloses absorbent structures that comprise superabsorbent polymers, optionally a cellulosic material, and at least a pair of substantially longitudinally extending channels. The core wrap can be adhesively bonded through the channels to form a channel bond, whose integrity is at least partially maintained both in dry and wet state. As the absorbent structure absorbs liquid and swells, the absorbent structure takes a three-dimensional shape with the channels becoming visible. The channels are indicated to provide improved fit and/or better liquid acquisition/transportation, and/or improved performance throughout the use of the absorbent structure.

Figure 5A:
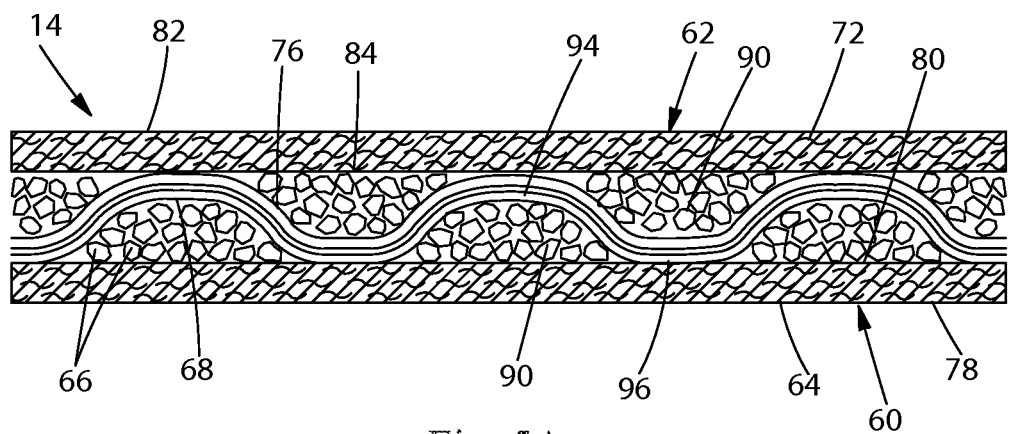
FIG. 5A is a partial sectional view of an absorbent core comprising a combination of first and second absorbent core layers described herein.
Figure 5B:
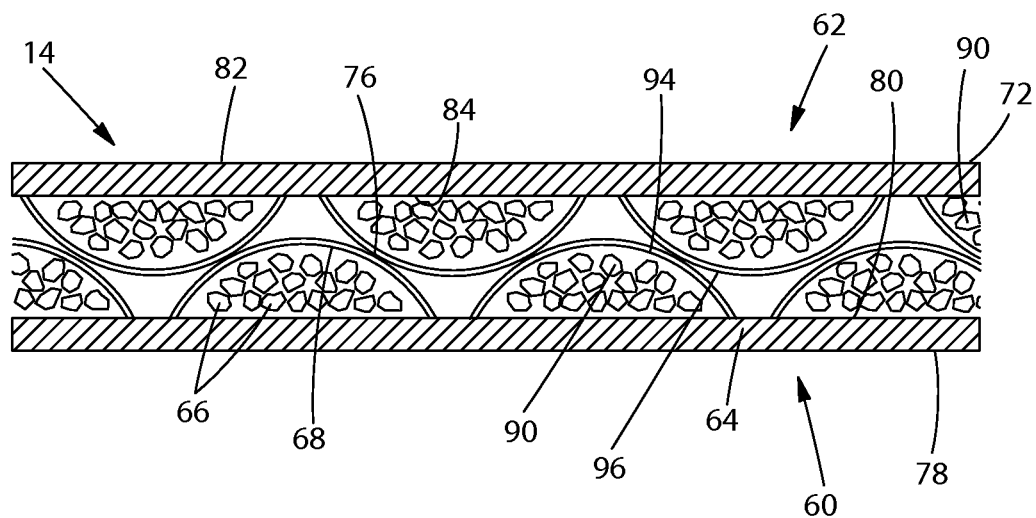
FIG. 5B is a partial sectional view of an absorbent core comprising a combination of the first and second absorbent core layers described herein.

As shown in FIGS. 5A, and 5B, the first and second layers 60 and 62 may be combined to form the absorbent core 14. The absorbent core 14 has an absorbent particulate polymer material area (not shown). The extent and shape of the absorbent particulate polymer material area may vary depending on the desired application of the absorbent core 14 and the particular absorbent article in which it may be incorporated. In some embodiments, the absorbent particulate polymer material area extends substantially entirely across the absorbent core 14. In some embodiments, absorbent particulate polymer material 66 and 74 is substantially continuously distributed across the absorbent particulate polymer material area.

The amount of absorbent particulate polymer material 66 and 74 present in the absorbent core 14 may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In some embodiments, the absorbent core 14 consists essentially of the first and second substrates 64 and 72, the absorbent particulate polymer material 66 and 74, and the thermoplastic adhesive composition 68 and 76. In some embodiments, the absorbent core 14 may be substantially cellulose free.

The absorbent particulate polymer material area may have a relatively narrow width in the crotch area of the absorbent article for increased wearing comfort. Hence, the absorbent particulate polymer material area may have a width as measured along a transverse line which is positioned at equal distance to the front edge and the rear edge of the absorbent article, which is less than about 100 mm, 90 mm, 80 mm, 70 mm, 60 mm or even less than about 50 mm.

It some absorbent articles, such as diapers, liquid discharge from the wearer may occur predominately in the front half of the diaper. The front half of the absorbent core 14 may therefore comprise most of the absorbent capacity of the core. Thus, according to certain embodiments, the front half of said absorbent core 14 may comprise more than about 60% of the superabsorbent material, or more than about 65%, 70%, 75%, 80%, 85%, or 90% of the superabsorbent material.

In certain embodiments, the absorbent core 14 may further comprise any absorbent material that is generally compressible, conformable, non-irritating to the wearer's skin, and capable of absorbing and retaining liquids such as urine and other certain body exudates. In such embodiments, the absorbent core 14 may comprise a wide variety of liquid-absorbent materials commonly used in disposable diapers and other absorbent articles such as comminuted wood pulp, which is generally referred to as airfelt, creped cellulose wadding, melt blown polymers, including co-form, chemically stiffened, modified or cross-linked cellulosic fibers, tissue, including tissue wraps and tissue laminates, absorbent foams, absorbent sponges, or any other known absorbent material or combinations of materials. The absorbent core 14 may further comprise minor amounts (typically less than about 10%) of materials, such as adhesives, waxes, oils and the like. Exemplary absorbent structures for use as the absorbent assemblies are described in U.S. Pat. Nos. 4,610,678; 4,834,735; 4,888,231; 5,260,345; 5,387,207; 5,397,316; and 5,625,222.

Figure 4:
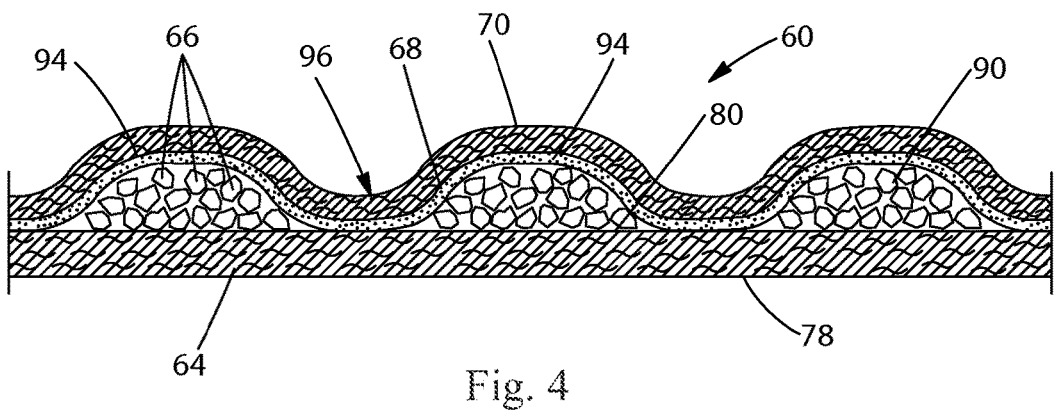
FIG. 4 is a partial cross sectional view of an absorbent core layer.

The thermoplastic adhesive material 68 and 76 may serve to cover and at least partially immobilize the absorbent particulate polymer material 66 and 74. In some embodiments, the thermoplastic adhesive material 68 and 76 can be disposed essentially uniformly within the absorbent particulate polymer material 66 and 74, between the polymers. In some embodiments, the thermoplastic adhesive material 68 and 76 may be provided as a fibrous layer which is at least partially in contact with the absorbent particulate polymer material 66 and 74 and partially in contact with the substrate layers 64 and 72 of the first and second absorbent layers 60 and 62. FIGS. 3 and 4 show such a structure wherein the absorbent particulate polymer material 66 and 74 is provided as a discontinuous layer, and a layer of fibrous thermoplastic adhesive material 68 and 76 is laid down onto the layer of absorbent particulate polymer material 66 and 74, such that the thermoplastic adhesive material 68 and 76 is in direct contact with the absorbent particulate polymer material 66 and 74, but also in direct contact with the second surfaces 80 and 84 of the substrates 64 and 72, where the substrates are not covered by the absorbent particulate polymer material 66 and 74. This imparts an essentially three-dimensional structure to the fibrous layer of thermoplastic adhesive material 68 and 76, which in itself is essentially a two-dimensional structure of relatively small thickness, as compared to the dimension in length and width directions. In other words, the thermoplastic adhesive material 68 and 76 undulates between the absorbent particulate polymer material 68 and 76 and the second surfaces of the substrates 64 and 72.

Thereby, the thermoplastic adhesive material 68 and 76 may provide cavities to cover the absorbent particulate polymer material 66 and 74, and thereby immobilizes this material. In a further aspect, the thermoplastic adhesive material 68 and 76 bonds to the substrates 64 and 72 and thus affixes the absorbent particulate polymer material 66 and 74 to the substrates 64 and 72. Thus, in accordance with certain embodiments, the thermoplastic adhesive material 68 and 76 immobilizes the absorbent particulate polymer material 66 and 74 when wet. Some thermoplastic adhesive materials will also penetrate into both the absorbent particulate polymer material 66 and 74 and the substrates 64 and 72, thus providing for further immobilization and affixation. Of course, while the thermoplastic adhesive materials disclosed herein provide a much improved wet immobilization (i.e., immobilization of absorbent material when the article is wet or at least partially loaded), these thermoplastic adhesive materials may also provide a very good immobilization of absorbent material when the absorbent core 14 is dry. The thermoplastic adhesive material 68 and 76 may also be referred to as a hot melt adhesive.

In accordance with certain embodiments, the thermoplastic adhesive material 68 and 76 may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic adhesive material may be a hot melt adhesive comprising at least one thermoplastic polymer in combination with other thermoplastic diluents such as tackifying resins, plasticizers and additives such as antioxidants. In certain embodiments, the thermoplastic polymer may have a molecular weight (Mw) of more than 10,000 and a glass transition temperature (Tg) usually below room temperature or −6° C.>Tg<16° C. In certain embodiments, typical concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)$_n$ radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of $C_2$ to $C_8$ alpha olefins.

In exemplary embodiments, the tackifying resin may have a Mw below 5,000 and a $T_g$ usually above room temperature, typical concentrations of the resin in a hot melt are in the range of about 30 to about 60%, and the plasticizer has a low Mw of typically less than 1,000 and a $T_g$ below room temperature, with a typical concentration of about 0 to about 15%.

In certain embodiments, the thermoplastic adhesive material 68 and 76 is present in the form of fibers. In some embodiments, the fibers may have an average thickness of about 1 to about 50 micrometers or about 1 to about 35 micrometers and an average length of about 5 mm to about 50 mm or about 5 mm to about 30 mm. To improve the adhesion of the thermoplastic adhesive material 68 and 76 to the substrates 64 and 72 or to any other layer, in particular any other nonwoven layer, such layers may be pre-treated with an auxiliary adhesive.

The absorbent core 14 may also comprise an auxiliary adhesive which is not illustrated in the figures. The auxiliary adhesive may be deposited on the first and second substrates 64 and 72 of the respective first and second absorbent layers 60 and 62 before application of the absorbent particulate polymer material 66 and 74 for enhancing adhesion of the absorbent particulate polymer materials 66 and 74 and the thermoplastic adhesive material 68 and 76 to the respective substrates 64 and 72.

The auxiliary glue may also aid in immobilizing the absorbent particulate polymer material 66 and 74 and may comprise the same thermoplastic adhesive material as described hereinabove or may also comprise other adhesives including but not limited to sprayable hot melt adhesives, such as H.B. Fuller Co. (St. Paul, Minn.) Product No. HL-1620-B. The auxiliary glue may be applied to the substrates 64 and 72 in various ways. For example, in some embodiments, the auxiliary glue may be applied in about 0.5 to about 1 mm wide slots spaced about 0.5 to about 2 mm apart.

The cover layer 70 shown in FIG. 4 may include the same material as the substrates 64 and 72, or may include a different material. In certain embodiments, the materials of the cover layer 70 are the nonwoven materials, such as the materials described above as useful for the substrates 64 and 72.

Although much of the present discussion is presented in the context of absorbent articles in form of diapers, it is to be appreciated that other absorbent articles, such as sanitary napkins can also be assembled with the topsheets and associated components as disclosed herein. Absorbent articles, such as sanitary napkins may be designed to be worn in close proximity to the crotch of the wearer. Such absorbent articles need to provide for fluid acquisition and retention and may look aesthetically pleasing, as well as be comfortable to wear. Examples of sanitary napkins are provided in U.S. Patent Publication Nos. 2010/0036339; 2010/0036347; and 2010/0036349, the disclosures of which are herein incorporated by reference. In use, sanitary napkins are stressed by a variety of fluid handling demands. Given the variety of fluid handling demands placed on different portions of an absorbent article, such as a sanitary napkin, the different physical interactions between portions of an absorbent article and portions of a wearer's body, and different moisture and chemical environments of different portions of a wearer's crotch region, there is continuing and unaddressed need for absorbent articles having aesthetically appealing, are comfortable to wear, but do not compromise the performance of the absorbent article. Sanitary napkins made with the topsheets described herein provide an aesthetically appealing surface to the body facing side of the article while not unduly compromising the performance of the acquisition layer and maintaining the comfort of the article during wearing.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one embodiment, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

Fastening Component

As described above, the disposable article may comprise a fastener 46. Fastener 46 may have a fastener zone that includes a fastener disposed at or near its outboard end. In one example, a fastener may be a patch of hook material constituting the hook components of a hook-and-loop fastening system. In this example, the garment-facing surface of front waist region may have a laterally extended landing zone bearing a patch or strip of loop material constituting the cooperating loop component of the hook-and-loop fastening system. Other examples may include any other cooperating engaging and receiving surfaces or components adapted to effect fastening, respective components of which may be disposed on either the fastening zone or the landing zone, or another location of the absorbent article as desired, as long as they provide for the adjustability of the waist opening size and snugness of the absorbent article, e.g. diaper, as it is being applied to a wearer. Suitable components of fastening systems for use herein, methods of manufacture, and materials suitable for use are generally described in the following: USPA 2010/0280484A1, U.S. Pat. No. 8,226,626, U.S. Pat. No. 8,168,853, and U.S. Pat. No. 8,193,407. Examples of stretch laminates that may be suitable for forming the elastic/stretch member (ear tab) are described in WO 05/110731 and USPA Nos. US 2004/0181200 and US 2004/0193133.

Figure 6A:
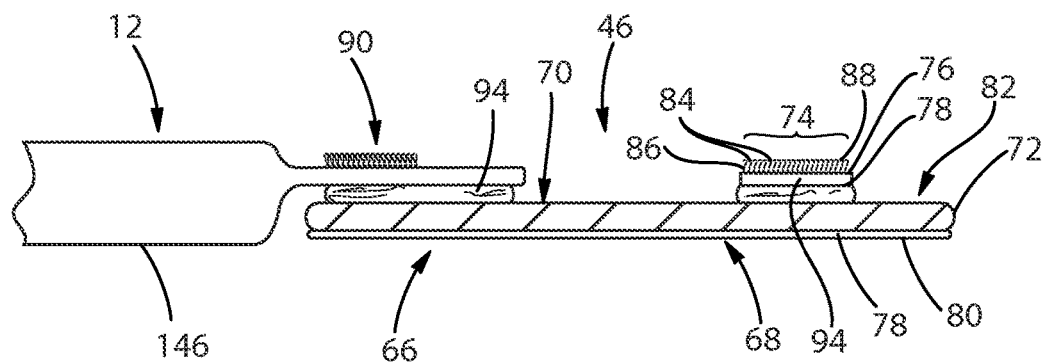
FIG. 6A is a cross-sectional view of the upper right hand corner of the diaper of FIG. 1, the view illustrating one embodiment of a fastener in an "open" position.

Referring to FIG. 6A, the fastener 46 is fixable to the diaper 10 and is positioned on the outside surface 146 of the body portion 12 of the diaper 10. Such positioning may be directly on the body portion or may be on the panels (ear tabs) in the first end region, one adjacent each longitudinal edge, so as to engage the landing member disposed in the second end region. The fastener 46 is fixed to the body portion 12 and, in an embodiment, has a length (i.e. in the lateral direction) from 40 to 60 mm, preferably from 45 to 55 mm, more preferably 46, 48, or 50 mm. In an embodiment, fastener 46 has a width (i.e. in the longitudinal direction) from 20 to 40 mm, preferably from 25 to 35 mm, more preferably 28, 30, or 32 mm.

Figure 6B:
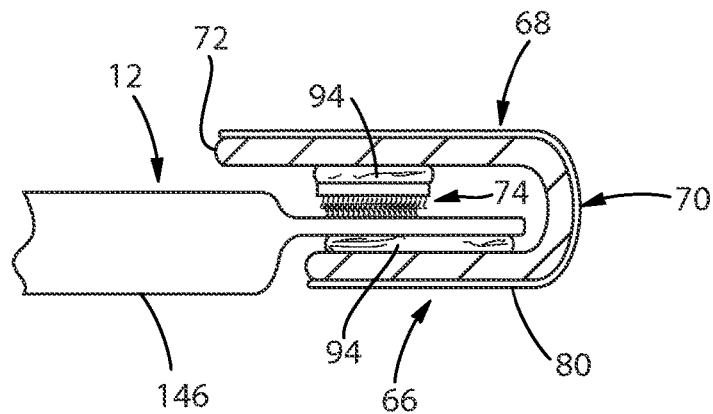
FIG. 6B is a cross-section view of the fastener of FIG. 6A in a "closed" position.
Figure 6C:
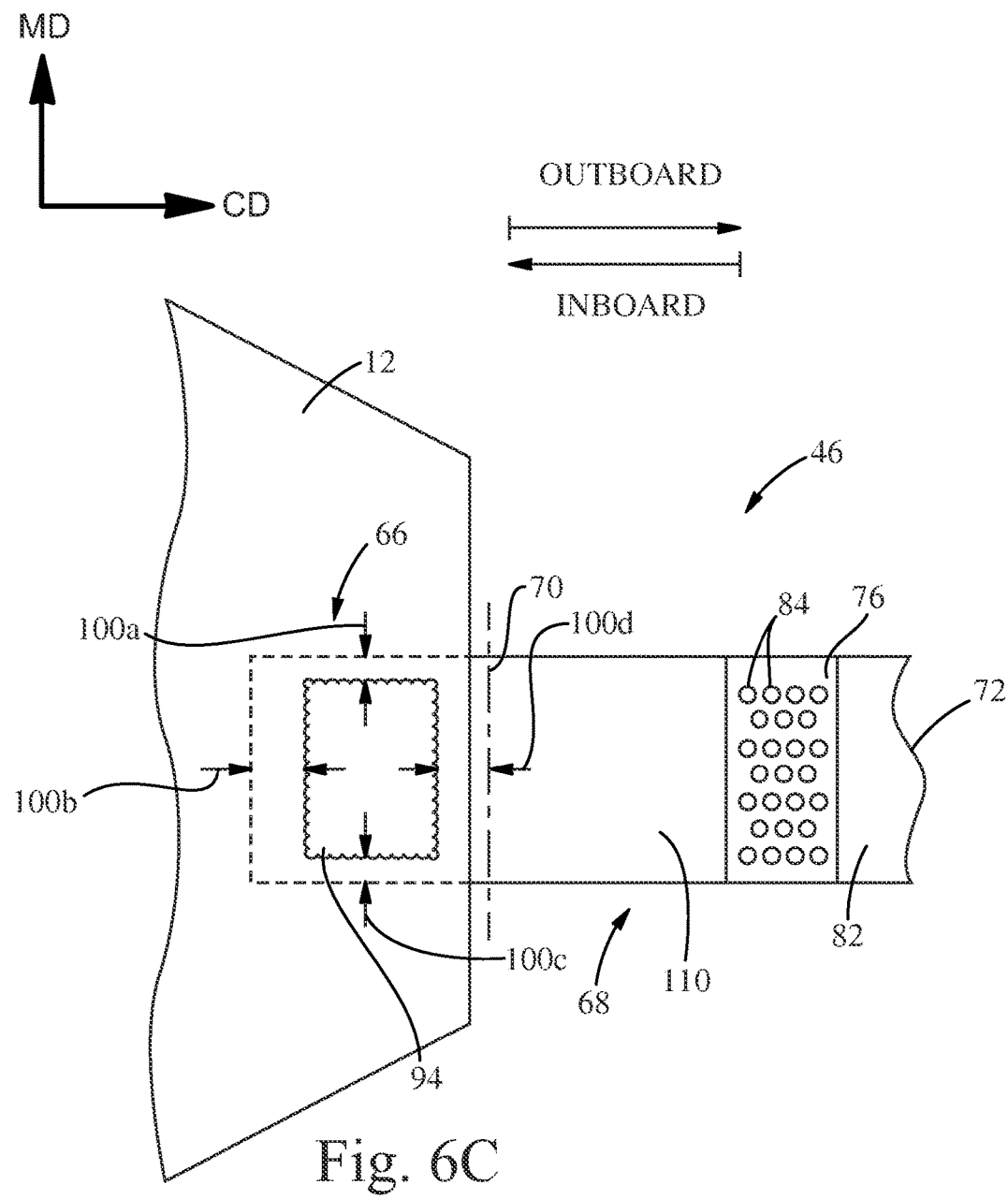
FIG. 6C is a top plan view of the fastener of FIG. 6A.
Figure 6D:
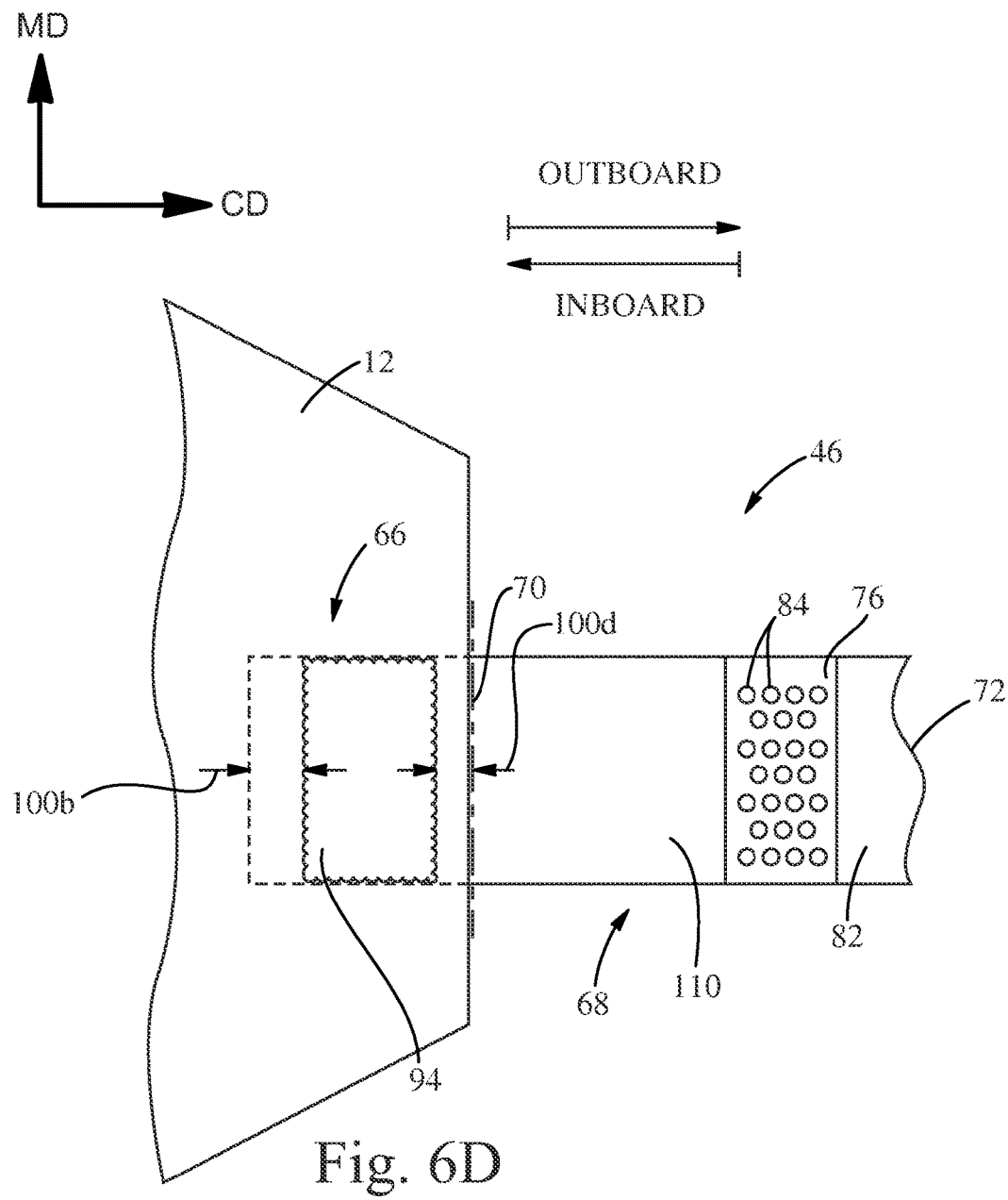
FIG. 6D is a top plan view of another embodiment of the fastener of FIG. 6A.

With reference to FIGS. 6A, 6B, 6C, and 6D, the fastener 46 may preferably be free of a release tape, and includes a fixed portion 66 attachable (and shown as attached) to the diaper 10, a connective portion 68 joined to and contiguous with the fixed portion 66, and a folding line 70 disposed between the fixed and connective portions 66 and 68, respectively. In some embodiments, the distance between folding line 70 and the line formed where the outboard edge of body 12 overlaps fastener 46 may be 3 mm or less, preferably 2 mm or less, more preferably 1 mm or less. In another embodiment, folding line 70 may be in common with the line formed where the outboard edge of body 12 overlaps fastener 46, as shown in FIG. 6D. The connective portion 68 includes a distal edge 72. The connective portion 68 also includes a fastening member 74 having a fastening surface 76 and a bonding surface 78 opposite to the fastening surface 76, wherein the fastening surface 76 is releasably fastenable to a portion of the diaper 10, in certain embodiments, to the landing member of the diaper 10 and also (optionally) a layer 90 of napped nonwoven fabric on the article adjacent the fastener, as shown in FIG. 6B. Independently, each of the connective portion 68 and the fixed portion 66 may also include a backing member 80 attached to the bonding surface 78 of the fastening member 74.

The connective portion 68 of the fastener 46 may also include a grip space 82, being substantially free of adhesive or other fastener attachment means, disposed adjacent to and between the fastening member 74 and the distal edge 72. The grip space 82 may make it easier for the user to grasp the fastener when the diaper 10 is to be fitted and attached to the wearer. In some embodiments, the grip space is substantially free or free of adhesive or other fastener attachment means.

As shown in FIG. 6A, the fastening member 74 may include a plurality of engaging elements 84 outwardly extending from the fastening surface 76. As shown, each engaging element 84 includes a stem 86 supported at one end by the fastening surface 76 and a head 88 disposed at the stem 86 end opposite the fastening surface 76. In an embodiment, the plurality of engaging elements are applied in a rectangularly shaped patch.

Connective portion 68 may comprise an adhesive-free zone 110. The adhesive-free zone may extend from folding line 70 to the inboard edge of fastening member 74, and have a width 112 of 8 mm or less, preferably 6 mm or less, more preferably 4 mm or less, more preferably 2 mm or less. In some embodiments, the adhesive-free zone may extend from the outboard edge of fastener means 94 to the inboard edge of fastening member 74.

FIG. 6B is a cross-sectional view of the fastener of FIG. 6A shown in a "closed" position, for example, prior to the article's use by the diaper wearer. In FIG. 6B, the connective portion 68 is folded along the folding line 70 onto a portion of the diaper 10 to permit the fastening member 74 to releasably fasten to the diaper 10. Optionally, as shown in FIG. 6B, the portion of the diaper 10 onto which the connective portion 68 is folded includes a layer 90 of napped nonwoven fabric. In some embodiments, the fastening member 74 releasably fastens to the topsheet, an ear (if present), or any other nonwoven disposed upon the lateral edge of the diaper. The layer 90 of napped nonwoven fabric can complementarily engage the engaging elements 84 on the fastening member 74. When ready for use, the fastening member 74 may be disengaged from the layer 90 of napped nonwoven fabric or other material to which it has been releasably fastened. When folded, the fastener 46 may have an additional frangible bond with the ear tab. This additional bond may be achieved by placing a small amount of adhesive, e.g. an adhesive dot, on the fastener 46—either directly on the fastener 46 or on the hooks (if present) on the fastening member 74.

FIG. 6C is a top plan view of the fastener illustrated in FIGS. 6A and 6B. In FIG. 6C, however, the fastener 46 is shown in an "open" position (as it is in FIG. 6A). The fixed portion 66 is beneath the overlapping body portion 12, and connecting the two to each other is fastener attachment means 94, preferably an adhesive.

With continued reference to FIGS. 6A and 6B, the fixed portion 66 of the fastener 46 is fixed to the outside surface of the body portion 12 to create a manufacturer's end (i.e., that attachment of the fastener 46 to the diaper 10 made during manufacture of the diaper 10). The connective portion 68 is that portion of the fastener 46 releasably fastenable to the landing member by the user when securing the diaper 10 on the wearer, and releasably fastenable to the layer 90 of napped nonwoven fabric, or other material as described above, when manufactured, shipped and stored prior to use. The connective portion 68, thus, forms the user's end as it is manipulated by the user to open the fastener 46 from its closed position, and to secure it to the landing member, thereby securing the diaper 10 to the wearer. Additionally, the outer surface of the fixed portion 66 and the outer surface of the connective portion 68 form the backing member 80 of the fastener 46.

The fixed portion 66 and the connective portion 68 can each be separate tapes which meet and are joined adjacent the longitudinal edge 40 of the body portion 12 in an area of joinder. However, a more practical structure for the fastener 46 is one in which the connective portion 68 and the fixed portion 66 are a unitary strip of tape material.

FIGS. 6A and 6B also show fastener attachment means 94 for fixing the fastener 46 to the body portion 12. These fastener attachment means 94 are any of those attachment means capable of providing an adequate bond, such as, for example, heat bonds, pressure bonds, ultrasonic bonds, dynamic mechanical bonds, or any other suitable attachment means or combinations of these attachment means as are known to those of ordinary skill in the art. The fastener attachment means 94 may include any of those adhesives capable of providing an adequate bond with other portions of the diaper, and may be a pressure-sensitive adhesive, such as code number XPF 1.42.34 available from The 3M Company (St. Paul, Minn.). The use of adhesives that are not pressure sensitive adhesives is also contemplated. In one embodiment, the fastener attachment means is an ultrasonic bond. Suitable methods for ultrasonic bonding are described in Schaefer U.S. Pat. No. 4,430,148 and Willhite, Jr. et al. U.S. Pat. No. 4,823,783. Suitable equipment for ultrasonic bonding is available from Branson Ultrasonics Corporation of (Danbury, Conn.). High-pressure or ultrasonic bonding has been found to suitably fix the fastener to the article, especially, where the fastener is being attached to a layer of nonwoven fabric (e.g., spunbond-meltblown-spunbond (SMS) fibers) on the article.

In some embodiments, the fastener attachment means 94 is an adhesive applied to the fixed portion of the fastener such that it is offset from each of the edges of the fixed portion that are overlapped by body portion 12, including the edge formed by folding line 70, as is shown in FIG. 6C, as denoted by offsets 100a, 100b, 100c, and 100d. In an embodiment, as shown in FIG. 6D, the adhesive is applied to the fixed portion of the fastener such that it is offset from each of the lateral edges of the fixed portion including the edge formed by the folding line, as is shown in FIG. 6C, as denoted by offsets 100b and 100d, i.e. 100a and 100c are reduced to zero.

In some embodiments, the attachment means, which may be an adhesive, covers from 15% to 90% of the surface of the fixed portion of the fastener that will be overlapped by the body portion of the article once attached to the article, prior to the fastener and the article being mechanically bonded to each other, preferably from 35% to 90%, more preferably from 65% to 85%. In yet other embodiments, the attachment means, which may be an adhesive, covers from 20% to 95% of the surface of the fixed portion of the fastener that will be overlapped by the body portion of the article once attached to the article, after the fastener and the article being mechanically bonded to each other, preferably from 40% to 95%, more preferably from 70% to 90%.

In some embodiments, attachment means 94, which may be an adhesive, may be applied in a rectangularly shaped patch, as shown in FIG. 6C. The patch may have edges that are substantially parallel to one or more of (a) the leading edge (MD) of the fastener, (b) the trailing edge (MD) of the fastener, (c) the inboard edge (CD) of the fastener, and (d) the folding line 70.

In some embodiments, the adhesive may be applied in a patch and the portion of the adhesive patch proximate to the leading edge (MD) of the fastener has a substantially straight edge, which is substantially parallel to the leading edge (MD) of the fastener. The substantially straight edge of the adhesive patch may be offset from the leading edge (MD) of the fastener by 0.1 mm to 8 mm, preferably from 0.25 mm to 6 mm, more preferably from 0.5 mm to 2 mm. The substantially straight edge of the adhesive patch may be offset from the leading edge (MD) of the fastener by 8 mm or less, preferably 6 mm or less, more preferably 2 mm or less. In another embodiment, the substantially straight edge of the adhesive patch is not offset from the leading edge (MD) of the fastener.

In some embodiments, the adhesive may be applied in a patch and the portion of the adhesive patch proximate to the trailing edge (MD) of the fastener has a substantially straight edge, which is substantially parallel to the trailing edge (MD) of the fastener. The substantially straight edge of the adhesive patch may be offset from the trailing edge (MD) of the fastener by 0.1 mm to 8 mm, preferably from 0.25 mm to 6 mm, more preferably from 0.5 mm to 2 mm. The substantially straight edge of the adhesive patch may be offset from the trailing edge (MD) of the fastener by 8 mm or less, preferably 6 mm or less, more preferably 2 mm or less. In another embodiment, the substantially straight edge of the adhesive patch is not offset from the trailing edge (MD) of the fastener.

In some embodiments, the adhesive may be applied in a patch and the portion of the adhesive patch proximate to the folding line of the fastener has a substantially straight edge, which is substantially perpendicular to the leading edge (MD) of the fastener. The substantially straight edge of the adhesive patch may be offset from the folding line by 0.1 mm to 4 mm, preferably from 0.25 mm to 2 mm, more preferably from 0.5 mm to 1 mm. The substantially straight edge of the adhesive patch may be offset from the folding line by 4 mm or less, preferably 2 mm or less, more preferably 1 mm or less.

In some embodiments, the adhesive may be applied in a patch and the portion of the adhesive patch proximate to the inboard edge of the fixed portion of the fastener has a substantially straight edge, which is substantially perpendicular to the leading edge (MD) of the fastener. The substantially straight edge of the adhesive patch may be offset from the inboard edge of the fixed portion by 0.1 mm to 4 mm, preferably from 0.25 mm to 2 mm, more preferably from 0.5 mm to 1 mm. The substantially straight edge of the adhesive patch may be offset from the inboard edge of the fixed portion by 4 mm or less, preferably 2 mm or less, more preferably 1 mm or less.

In some embodiments, fastener attachment means 94 will be a combination of at least two means of providing an adequate bond. For example, an adhesive may be applied to create an initial bond, and subsequently, a mechanical bond may be formed over the same area. In some embodiments, the adhesive is applied to the fixed portion prior to the fastener being introduced to the converting line, where the term "prior" includes at any time before the fastener is fed into the line, for example the fastener tape being manufactured independently of the assembly of the absorbent article to which it will ultimately be attached. In some embodiments, the adhesive is applied online during the converting process, e.g. a fastening tape is fed into the converting line being substantially free of such adhesive, the adhesive is applied on the line, and then the then-adhesive-bearing fastener is attached to other diaper components. It is contemplated that the adhesive may be applied to the body portion prior to the fixed portion of the fastener being attached to the article, or that the adhesive is applied to the fixed portion of the fastener prior to being attached to the body portion.

As shown and described above, the inner surface of the fixed portion 66 is affixed to the outside surface of the body portion 12 by a fastener attachment means 94. The connective portion 68 is provided with a fastening member 74 joined to it by another fastener attachment means 94, although an adhesive attachment means may be placed on the fastening member 74 separately and the combined material joined to the connective portion 68.

Materials for the fastener can include a tape material such as tape code numbers XPF 14.43.0, Y-9376, or Y-9030, available under the trade name CFT-00104, from The 3M Company (St. Paul, Minn.). The tape materials in the various embodiments disclosed herein are a polyethylene film having a fastener attachment means tailored to bond to the polyethylene positioned on the tape material.

The fastening member 74 of the fastener 46 forms a closure between the fastener 46 and the landing member. More specifically, the engaging elements 84 of fastening member 74, in one embodiment, engage a complementary fastening surface of the landing member to maintain the first end region and the second end region in an overlapping configuration to provide a secure side closure. As discussed in more detail below, the fastening surface 76 may include any of the known means for achieving a closure such as buttons, snaps, hook fastening materials, or loop fastening materials. In one specific embodiment, however, the fastening surface 76 includes loop fastening materials. As used herein, the term "hook fastening material" is used to designate a material having engaging elements 84. The hook fastening material may also be referred to as a male fastener.

It should also be understood that the use of the term "hook" should be non-limiting in the sense that the engaging elements 84 may comprise any shapes as are known in the art so long as they are adapted to engage a complementary fastening surface 76 of the landing member, for example. The hook fastening materials are intended to engage fibrous elements of a loop fastening material so as to provide a secure fastening system. Thus, the hook fastening material may be manufactured from a wide range of materials. Suitable materials include nylon, polyester, polypropylene, or any combination of these materials. A suitable hook fastening material includes a number of shaped engaging elements 84 projecting from a woven backing such as the commercially available material designated "Scotchmate" brand No. FJ3402 available from The 3M Company (St. Paul, Minn.). Alternatively, the engaging elements may have any shape such as hooks, "T's" or any other shape as are well known in the art. A suitable hook fastening material is described in Scripps U.S. Pat. No. 4,846,815.

As described above, the fastening member may comprise a plurality of engaging elements outwardly extending from the fastening surface. In some embodiments, the plurality of engaging elements are applied in a patch. In some embodiments, the portion of the engaging elements patch proximate to the folding line of the fastener has a substantially straight edge, which is substantially perpendicular to the leading edge (MD) of the fastener, and the cross-direction distance from the substantially straight edge to the folding line is 8 mm or less, preferably 6 mm or less, more preferably 4 mm or less, more preferably 2 mm or less. In some embodiments, the ratio of the machine direction dimension of the engaging elements patch and the cross-direction dimension of the engaging elements patch is at least 1.8 to 1, preferably at least 2 to 1, more preferably at least 2.2 to 1.

In some embodiments, the ratio of the machine direction length of the engaging elements patch and the cross-direction distance from the substantially straight edge to the folding line is at least 4 to 1, preferably at least 5 to 1, more preferably at least 8 to 1.

The fastening member 74 may be a separate member fixed to and associated with the fastener 46 or a unitary member with the fastener 46. The fastening member 74 may be directly attached to the connective portion 68 or may be indirectly attached to the connective portion 68, such as by attaching the fastening member 74 to an intermediate member which, in turn, is attached to the connective portion 68. In one embodiment, as shown in FIGS. 6A and 6B, the fastening member 74 is directly fixed to the connective portion 68 of the fastener 46 by the fastener attachment means 94. The fastener 46 may be positioned in the panels (also referred to as ear tabs) of the first end region adjacent the longitudinal edges. In some embodiments, the fastening member 74 may be disposed on a first area (or portion) of the connective portion 68 adjacent the distal edge 72 of the fastener 46.

In some embodiments, the fastener may comprise both an adhesive and a plurality of engaging members, as described herein. In such embodiments, the fastener may have a bending stiffness, measured in the machine direction (MD), of about 0.3 N/mm or greater, preferably about 0.4 N/mm or greater, more preferably about 0.5 N/mm or greater. In such embodiments, the fastener may also or alternatively, have a tensile strength, measured in the machine direction (MD), of about 0.02 N/mm or greater, preferably about 0.025 N/mm or greater, more preferably about 0.03 N/mm or greater. Further, in such embodiments, the fastener may also or alternatively, have a tensile strength, measured in the cross direction (CD), of about 0.03 N/mm or greater, preferably about 0.035 N/mm or greater, more preferably about 0.04 N/mm or greater.

In an embodiment, an ink-based graphic is applied to a visibly exposed surface of the fastener, preferably wherein the graphic communicates fastening to a user or a caregiver, more preferably wherein the graphic is a button.

The landing member (if present) provides a means for securing itself and the fastener 46 together to provide a secure side closure and to maintain the first end region and the second end region in an overlapping configuration. The landing member may be disposed anywhere on the diaper 10 so long as it engages the fastener 46 to provide the side closure. For example, the landing member may be disposed on the outside surface in the second end region, or on any other portion of the diaper 10 which is disposed to engage the fastener 46. In addition, the landing member may be a unitary piece of material that is neither divided nor discontinuous with an element of the diaper 10 such as the topsheet or the backsheet.

Tensile Strength Test Method

Figure 7:
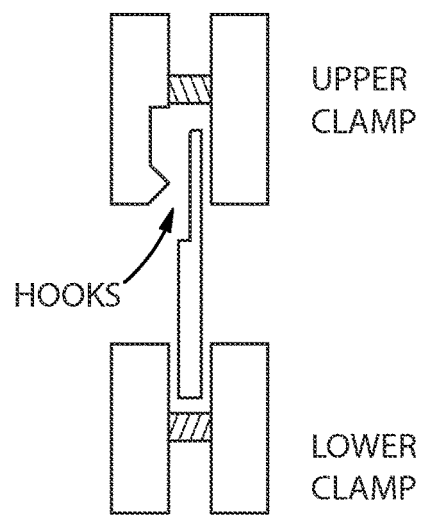
FIG. 7 is a front view of a sample being placed in an apparatus for tensile strength testing according to the test method described herein.

The fastening tapes of the invention may be measured for their tensile strength according to the method disclosed herein, which is based on the standard ASTM D 638 method, with a crosshead speed of 30 mm/s, using a tensile tester with at least a 50 Hz data acquisition rate. Placement of the sample into the apparatus, as described below, is depicted in FIG. 7.

Sample Preparation:
1. Cut the fastening tape out of the back ear, being careful not to cut through the release tape (if present). Some back ear laminate may remain attached to the tape.

Loading the Sample into the Test Apparatus:
1. Open the clamps.
2. Insert the portion of the tape that is bonded to the back ear (or equivalent) into the lower clamp, so that approximately half of the bonded region is in the clamp. The hooks (if present) should face the operator.
3. Close the lower clamp, ensuring that the sample is parallel with the clamp, adjusting as necessary (see FIG. 7).
4. Start the tensile tester and data collection device simultaneously, as described by the manufacturer's instructions. Disregard any pre-test strain.

Measurement:
1. The instrument should operate until the entire specimen fails (breaks). The operator must verify that the instrument is operating until the entire specimen fails. If the test is terminated before the entire specimen fails or continues to run after the entire specimen fails, the break sensitivity should be adjusted accordingly, and the result of the incomplete test discarded.
2. The operator should watch the specimens during testing to check for slippage. Slippage of the specimen in the jaws may lead to incorrect values for the elongation. If slippage is observed during testing, the jaw air pressure should be increased in increments and testing repeated with a new specimen until no slippage is observed and the result of the failed test discarded. If the sample fails at the jaw or bar line, then another sample should be tested and the result of the failed test discarded.

Bending Stiffness Test Method

The fastening tapes of the invention may be measured for their bending stiffness according to the standard ASTM D 790 method, with a crosshead speed of 500 mm/min, using a tensile tester with at least a 400 Hz data acquisition rate. Hooks (if present) must be removed prior to testing, without damaging the remaining fastening tape. This may be achieved by using an ice spray, or by other conventional means.

EXAMPLES

The following examples may be useful in understanding the present disclosure.

The data shown in Tables 1 and 2, show results from measuring certain physical characteristics of fastening systems comprising fastening tapes as described below. Also shown are results of limited experimental testing with potential consumers of absorbent articles comprising the certain fastening systems. The samples include a fastening system according to the prior art, a comparative fastening system, and fastening systems according to the invention.

Tensile Strength (both in the machine direction (MD) and the cross direction (CD)) were measured according to the test methods set forth above. Limited experimental testing with potential consumers to generally evaluate the sample (e.g. samples according to the invention versus the prior art and/or each other) was conducted according to the procedure described below.

A fit-study may be conducted with at least 20 panelists per study, each panelist being a mother who is a potential consumer of absorbent articles. Panelists are instructed to apply a diaper with the respective fastener on her baby. The diapers are worn for 90 minutes. After this time, each panelist evaluates the perceived fit of the diaper, and based on position measurements the slippage of the diaper is measured. Each baby wears at least one diaper of each fastener being tested during the study. The results are analyzed and the differences are evaluated statistically. Consumer acceptance, as assessed by these panelists is determined based on the probability that a given product is not worse than the reference product, which is measured by the <p> value. In case the probability of a sample not being different from the reference sample is larger than 0.2, it is concluded that the products performed identically, i.e. there is no statistical difference. In case such probability is less than 0.05, but larger than 0.01, it is concluded that the product was not as good as the reference, but may still be sufficiently acceptable. In case such probability is less than 0.01, it is concluded that the product was below the acceptance limit for the potential consumer who has also used the reference product. In case such probability is between 0.2 and 0.05, additional evaluation may be required.

Sample A is a fastening system having a fastening tape according to the prior art, and comprising a release tab. Sample B is a fastening system having a fastening tape, being a comparative sample, and free of a release tape. Sample C is a fastening system having a fastening tape according to the invention, and free of a release tape. Sample D is a fastening system having a fastening tape according to the invention, and free of a release tape.

Sample A was made by applying a commercially available fastening tape to a diaper stretch ear on a diaper converting line. The tape is 46 mm lateral×26 mm longitudinal length tape (obtainable from 3M Corporation under the trade name CFT-00104 and related trade names). This tape consists of a nonwoven extrusion laminated to a poly film and contains a pressure sensitive adhesive. In addition to the adhesive attachment, the tape-to-ear bond was augmented with a mechanical bond. The Sample A fastener further comprises a release tape applied with its adhesive side overlapping both the diapers' ear and the fastening tape. This release tape is also obtainable from 3M Corporation under the trade name ERT-1075 and related trade names. Sample A also contained a 13 mm wide hook portion running the entire 26 mm longitudinal length of the tape. This hook was adhered to the tape by the pressure-sensitive adhesive on the underside of the hook substrate. Sample B was made with the same 3M fastening tape as Sample A, except that it did not contain the release tape. It also contains a 13 mm wide hook portion.

Samples C and D were made by applying a commercially available hot melt adhesive applied in a rectangular area onto the outer longitudinal edge of the stretch ear. An adhesive-free fastening tape was then contacted with this area causing the tape to adhere to the edge of the ear. This was done in such a way that no adhesive remained exposed after the tape was applied. The tape was 30 mm in longitudinal length×46 mm in width and consisted of a 50 gsm nonwoven extrusion laminated to a 30 gsm poly layer. Hook application was similar to Samples A and B. Samples C and D did not contain a release tape.

TABLE 1

| Sample | Release Tape | MD Tensile Strength (N/mm) | CD Tensile Strength (N/mm) | MD Bending Stiffness (N/mm) | Distance from Hook to Back Ear (mm) | Consumer Acceptance* vs. Sample A (<p> value)** |
|---|---|---|---|---|---|---|
| A | yes | 0.02 | 0.03 | 0.3 | 10 | n/a |
| B | no | 0.02 | 0.03 | 0.3 | 10 | <0.01 |

*As assessed by potential consumers
**p = 0.01 denotes a significantly lower result at a 99% confidence level Potential consumers were provided with diapers including fastening tapes according to Sample A and Sample B. As is evidenced by the <p> value, a significantly lower score of acceptance was recorded, for diapers including Sample B fastening tapes. The data show that when provided with diapers including fastening tapes that are otherwise similar, potential consumers preferred those having a release tape. As discussed above, simply removing the release tape from a fastening system is believed to cause undesirable effects. If not compensated for, then these undesirable effects reduce potential consumers' acceptance of the overall absorbent article that includes the fastening system.

TABLE 2

| Sample | Release Tape | MD Tensile Strength (N/mm) | CD Tensile Strength (N/mm) | MD Bending Stiffness (N/mm) | Distance from Hook to Back Ear (mm) | Consumer Acceptance* vs. Sample A (<p> value)** |
|---|---|---|---|---|---|---|
| A | yes | 0.02 | 0.03 | 0.3 | 10 | n/a |
| C | no | 0.03 | 0.04 | 0.5 | 10 | <0.05 |
| D | no | 0.03 | 0.04 | 0.5 | 4 | Not significant |

*As assessed by potential consumers
**p = 0.05 denotes a significantly lower result at a 95% confidence level Potential consumers were provided with diapers including fastening tapes according to Sample A, Sample C, and Sample D. As is evidenced by the <p> value, a significantly lower score of acceptance was recorded for diapers including Sample C fastening tapes, but not for Sample D fastening tapes. The data show that when provided with diapers including fastening tapes that are free of a release tape, potential consumers still preferred those with a release tape over those that compensated for some of the undesirable effects caused by removing the release tape; however, it should be noted that they still found the latter to be acceptable—just not as acceptable. When provided with diapers including fastening tapes that are free of a release tape, potential consumers expressed little difference in their preference for those with a release tape versus those that compensated for many of the undesirable effects caused by removing the release tape. Thus, in the absence of a release tape, it is demonstrated that compensatory factors are modifying the hook position relative to the back ear, the strength of the fastening tape, and the resistance to bending (bending stiffness) of the fastening tape. Without wishing to be bound by theory, it is believed that improving each of these factors provides a fit and/or cost benefit in the absence of a release tape individually, and also in combination with one or more of each other.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising a body portion and a fastener, the body portion comprising a liquid pervious topsheet, a liquid impervious backsheet joined to the topsheet, and a core disposed between the topsheet and the backsheet, the fastener comprising:
   (a) a fixed portion having an attached portion at which the fixed portion is attached to the body portion on an outside surface thereof, the fixed portion having an inboard edge, and being overlapped by the body portion to an overlapping outboard edge of the body portion, an adhesive in contact with the attached portion;
   (b) a connective portion joined to and contiguous with the fixed portion, the connective portion comprising:
      (i) a distal edge;
      (ii) a fastening member having a fastening surface and a bonding surface opposite to the fastening surface, wherein the fastening surface is releasably fastenable to the article;
      (iii) a backing member attached to the bonding surface of the fastening member; and
   (c) a folding line outboard of the attached portion;
wherein the adhesive is offset from each of the inboard edge of the fixed portion and outboard edge of the body portion.

2. The article according to claim 1, wherein a distance between the folding line and the overlapping outboard edge of the body portion is about 3 mm or less.

3. The article according to claim 2, wherein the distance is about 1 mm or less.

4. The article according to claim 1, wherein the folding line is coincident with the overlapping outboard edge of the body portion.

5. The article according to claim 1, wherein the fastener is free of a release tape.

6. The article according to claim 1, wherein the adhesive is applied to the body portion prior to the fixed portion of the fastener being attached to the article.

7. The article according to claim 1, wherein the adhesive is applied to the fixed portion of the fastener prior to being attached to the body portion.

8. The article according to claim 1, wherein the adhesive is a pressure-sensitive adhesive.

9. The article according to claim 1, wherein the adhesive is not a pressure-sensitive adhesive.

10. The article according to claim 1, wherein the adhesive covers from about 15% to about 90% of a surface area of the fastener overlapped by the body portion.

11. The article according to claim 10, wherein the adhesive covers from about 65% to about 85% of the surface area.

12. The article according to claim 1, wherein the adhesive covers from about 20% to about 95% of a surface area of the fastener overlapped by the body portion.

13. The article according to claim 12, wherein the adhesive covers from about 70% to about 90% of the surface area.

14. The article according to claim 1, wherein the adhesive is applied in a rectangularly shaped patch.

15. The article according to claim 1, wherein the fastener has a fastener upper edge and a fastener lower edge, the adhesive is applied in a patch extending to an adhesive upper edge proximate the fastener upper edge, and the adhesive upper edge is offset from the fastener upper edge by about 0.1 mm to about 8 mm.

16. The article according to claim 15, wherein the adhesive upper edge is offset from the fastener upper edge by about 0.5 mm to about 2 mm.

17. The article according to claim 15, wherein the adhesive upper edge is offset from the fastener upper edge by about 2 mm or less.

18. The article according to claim 1, wherein the fastener has a fastener upper edge and a fastener lower edge, the adhesive is applied in a patch extending to an adhesive lower edge proximate the fastener lower edge, and the adhesive lower edge is offset from the fastener lower edge by about 0.1 mm to about 8 mm.

19. The article according to claim 18, wherein the adhesive lower edge is offset from the fastener lower edge by about 0.5 mm to about 2 mm.

20. The article according to claim 19, wherein the adhesive lower edge is offset from the fastener lower edge by about 2 mm or less.

21. The article according to claim 1, wherein the fastener has a fastener upper edge and a fastener lower edge, the adhesive is applied in a patch extending to an adhesive lower edge proximate the fastener lower edge, and the adhesive lower edge is not offset from the fastener lower edge.

22. The article according to claim 1, wherein the adhesive is applied in a patch extending to an adhesive outboard edge that is offset from the folding line by about 0.1 mm to about 4 mm.

23. The article according to claim 22, wherein the adhesive outboard edge is offset from the folding line of the fastener by about 0.5 mm to about 1 mm.

24. The article according to claim 22, wherein the adhesive outboard edge is offset from the folding line of the fastener by about 1 mm or less.

25. The article according to claim 1, wherein the adhesive is applied in a patch extending to an adhesive inboard edge that is offset from the inboard edge of the fixed portion by about 0.1 mm to about 4 mm.

26. The article according to claim 25, wherein the adhesive inboard edge is offset from the inboard edge of the fixed portion by about 0.5 mm to about 1 mm.

27. The article according to claim 25, wherein the adhesive inboard edge is offset from the inboard edge of the fixed portion by about 1 mm or less.

28. The article according to claim 1, wherein the fastening surface is releasably fastenable to a layer of napped nonwoven fabric on the article.

29. The article according to claim 1, wherein the fastening surface is releasably fastenable to a surface of an ear attached to the article.

30. The article according to claim 1, wherein an ink-based graphic is applied to a visibly exposed surface of the fastener.

31. The article according to claim 30, wherein the graphic communicates fastening to a user or a caregiver.

32. The article according to claim 31, wherein the graphic is a button.

33. The article according to claim 1, wherein the adhesive is applied to the fixed portion of the fastener during the assembly of the absorbent article on a converting line.

34. The article according to claim 1, wherein the adhesive is applied to the fixed portion of the fastener prior to the assembly of the absorbent article on a converting line.

35. The article according to claim 1, wherein the article is selected from the group consisting of diapers, training pants, adult incontinence undergarments, and feminine hygiene products.

36. The article according to claim 35, wherein the article is a diaper.

37. A disposable absorbent article comprising a body portion and a fastener, the body portion comprising a liquid pervious topsheet, a liquid impervious backsheet joined to the topsheet, and a core disposed between the topsheet and the backsheet, the core being substantially cellulose free; the fastener comprising:
  (a) a fixed portion having an attached portion at which the fixed portion is attached to the body portion on an outside surface thereof, the fixed portion having an inboard edge, and being overlapped by the body portion to an overlapping outboard edge of the body portion, an adhesive in contact with the attached portion;
  (b) a connective portion joined to and contiguous with the fixed portion, the connective portion comprising:
    (i) a distal edge;
    (ii) a fastening member having a fastening surface and a bonding surface opposite to the fastening surface, wherein the fastening surface is releasably fastenable to the article;
    (iii) a backing member attached to the bonding surface of the fastening member; and
  (c) a folding line outboard of the attached portion;
wherein the adhesive is offset from each of the inboard edge of the fixed portion and outboard edge of the body portion.

* * * * *